(12) United States Patent
Hanlon et al.

(10) Patent No.: US 9,008,275 B2
(45) Date of Patent: Apr. 14, 2015

(54) VOLTAGE SWITCHING IN AN IMAGING MODALITY THAT UTILIZES RADIATION TO IMAGE AN OBJECT

(75) Inventors: Matthew Hanlon, Kingston, NH (US); Stephen J. Quigley, Hampstead, NH (US)

(73) Assignee: Analogic Corporation, Peabody, MA (US)

(*) Notice: Subject to any disclaimer, the term of this patent is extended or adjusted under 35 U.S.C. 154(b) by 420 days.

(21) Appl. No.: 13/461,332

(22) Filed: May 1, 2012

(65) Prior Publication Data
US 2013/0294578 A1 Nov. 7, 2013

(51) Int. Cl.
*H05G 1/32* (2006.01)
*H05G 1/46* (2006.01)
*H05G 1/58* (2006.01)
*A61B 6/00* (2006.01)

(52) U.S. Cl.
CPC . *H05G 1/46* (2013.01); *A61B 6/482* (2013.01); *A61B 6/56* (2013.01); *H05G 1/58* (2013.01)

(58) Field of Classification Search
USPC ............ 378/5, 101, 106, 108, 111, 112, 115, 378/104
See application file for complete search history.

(56) References Cited

U.S. PATENT DOCUMENTS

| | | | |
|---|---|---|---|
| 5,398,182 A | 3/1995 | Crosby | |
| 5,461,297 A | 10/1995 | Crawford | |
| 5,661,774 A | 8/1997 | Gordon et al. | |
| 7,256,637 B2 | 8/2007 | Iskander et al. | |
| 7,388,208 B2 | 6/2008 | Deych | |
| 7,742,573 B2 | 6/2010 | Caiafa et al. | |
| 7,792,241 B2 | 9/2010 | Wu et al. | |
| 7,826,587 B1 | 11/2010 | Langan et al. | |
| 8,031,831 B2 | 10/2011 | Zou | |
| 8,548,118 B2 * | 10/2013 | Hsieh et al. | 378/16 |
| 2009/0092219 A1 | 4/2009 | Wu et al. | |
| 2010/0104062 A1 | 4/2010 | Wu et al. | |
| 2011/0150175 A1 | 6/2011 | Hsieh et al. | |

* cited by examiner

*Primary Examiner* — Hoon Song
(74) *Attorney, Agent, or Firm* — Cooper Legal Group LLC (57) ABSTRACT

Among other things, one or more techniques and/or systems are provided for varying a voltage applied to a radiation source of an imaging modality to vary an energy of emitted radiation. A power supply comprises at least two rectifiers, with a first rectifier being electrically separated from a second rectifier via a switching component. When the switching component is opened, the first and second rectifiers are effectively arranged in parallel, and when the switching component is closed, the first and second rectifiers are effectively arranged in series. The voltage applied by the power supply may be different based upon whether the rectifiers are arranged in parallel or in series, but the power output by the power supply may remain substantially constant regardless of the rectifier arrangement.

20 Claims, 6 Drawing Sheets

VOLTAGE SWITCHING IN AN IMAGING MODALITY THAT UTILIZES RADIATION TO IMAGE AN OBJECT

BACKGROUND

The present application relates to the field of imaging and, in particular, imaging modalities that generate images utilizing radiation technology (e.g., at times referred to herein as radiation imaging modalities). It finds particular application with medical, security, and/or other applications where obtaining information about physical properties (e.g., density and/or effective atomic number, etc.) of an object under examination may be useful.

CT and other radiation imaging modalities (e.g., single-photon emission computed tomography (SPECT), mammography, digital radiography, etc.) are useful to provide information, or images, of interior aspects of an object under examination. Generally, the object is exposed to radiation photons (e.g., such as X-rays, gamma rays, etc.), and an image(s) is formed based upon the radiation absorbed and/or attenuated by the interior aspects of the object, or rather an amount of photons that is able to pass through the object. Traditionally, the image(s) that is formed from the radiation exposure is a density image or attenuation image, meaning the image is colored/shaded as a function of the respective densities of sub-objects comprised within the object under examination. For example, highly dense sub-objects absorb and/or attenuate more radiation than less dense sub-objects, and thus a sub-object having a higher density, such as a bone or metal, for example, may be shaded differently than less dense sub-objects, such as muscle or clothing.

While such imaging modalities have proven successful, imaging based upon more than density may be advantageous in some applications. For example, in security applications, certain threat items can be hidden amongst clothing or other non-threat items that have similar densities to the threat items. Thus, in some applications, such as airport security, it may be useful to determine other and/or additional physical properties of the item under examination, such as, for example, effective atomic number (e.g., at times also referred to as z-effective). In this way, threat items that have densities similar to non-threat items, but different atomic numbers, for example, can be correctly identified.

As early as 1992, multi-energy imaging modalities have been deployed in some environments, such as airport and military establishments, to provide additional information about an object under examination, such as an object's effective atomic number(s). These modalities have provided improved detection and false alarm performance when tasked to differentiate between sub-objects, relative to systems that merely differentiate sub-objects based upon density.

Multi-energy imaging modalities function by using multiple, distinct radiation photon energy spectra to reconstruct an image(s) of an object. Such distinct energy spectra can be measured using numerous techniques. For example, multi-energy measurements can be performed using energy resolving detectors (e.g., where the detectors are configured to selectively detect radiation having an energy within a first energy spectrum from radiation having an energy within a second energy spectrum), two radiation sources (e.g., respectively emitting radiation at a different energy level/spectrum), and/or by varying the voltage applied to a radiation source (e.g., such that the energy of emitted radiation varies as the applied voltage varies).

SUMMARY

Aspects of the present application address the above matters, and others. According to one aspect, a power supply configured to provide power to at least a radiation source of a radiation imaging modality is provided. The power supply is configured to substantially maintain a constant power output to the radiation source while varying a voltage applied to the radiation source such that the radiation source emits radiation at a first energy when a first voltage is applied to the radiation source and emits radiation at a second energy when a second voltage is applied to the radiation source.

According to another aspect, a method for emitting radiation at at least two different energies from a radiation modality is provided. The method comprises arranging two or more rectifiers of a power supply in parallel and supplying a first power at a first voltage to a radiation source based upon the parallel arrangement during a first interval of time. The method also comprises emitting radiation at a first energy based at least in part upon the first voltage being applied to the radiation source. The method further comprises arranging the two or more rectifiers of the power supply in series and supplying a second power at a second voltage to the radiation source based upon the series arrangement during a second interval of time. The method also comprises emitting radiation at a second energy based at least in part upon the second voltage being applied to the radiation source.

According to yet another aspect, a multi-energy imaging modality is provided. The imaging modality comprises a radiation source configured to emit radiation and a detector array configured to detect at least some of the emitted radiation that has traversed an object under examination. The imaging modality also comprises a power supply configured to provide power to at least the radiation source, the power supply configured to substantially maintain a constant power output while varying a voltage applied to the radiation source during an examination of the object.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques are described for varying a voltage supplied to a radiation source of an imaging modality, such as a multi-energy (e.g., dual-energy) CT scanner, for example. More particularly, a power supply comprising two or more rectifiers is described herein. The rectifiers are, at times, coupled in parallel and, at other times, coupled in series. The voltage and current output by respective rectifiers is typically held constant during an examination of an object (e.g., so as to substantially maintain a charge in a capacitor(s) of respective rectifiers), regardless of whether the rectifiers are coupled in series or parallel. However, by varying the coupling of the rectifiers (e.g., between a parallel arrangement and a series arrangement), the voltage output by the power supply (e.g., as opposed to respective voltages output by the different rectifiers) may be varied. For example, the voltage output by the power supply when the rectifiers are in series may be two times greater than the voltage output when the rectifiers are in parallel. Moreover, the current of the electrical signal output by the power supply when the rectifiers are in series may be approximately one-half of the current output by the power supply when the rectifiers are in parallel. In this way, an amount of power output by the power supply may be substantially constant (e.g., during a transition of the rectifier arrangement) despite changes in the output voltage.

It may be appreciated that such a power supply finds particular application in multi-energy imaging modalities that are configured to output two or more distinct energy spectrum (e.g., which may, for simplicity, be referred to herein as two or more energies) via a single radiation source. That is, such a power supply finds particular applicability in multi-energy imaging modalities that are configured to cause radiation to be emitted at two or more distinct energy spectrum by varying the voltage applied to the radiation source. Given that the charge in the capacitor(s) of respective rectifiers is substantially maintained while varying the voltage, the transition time for transitioning between a first voltage and a second voltage output by the power supply may be reduced (e.g., relative to a transition time of power supplies that are configured to alter an output voltage by charging/discharging capacitors).

Figure 1:
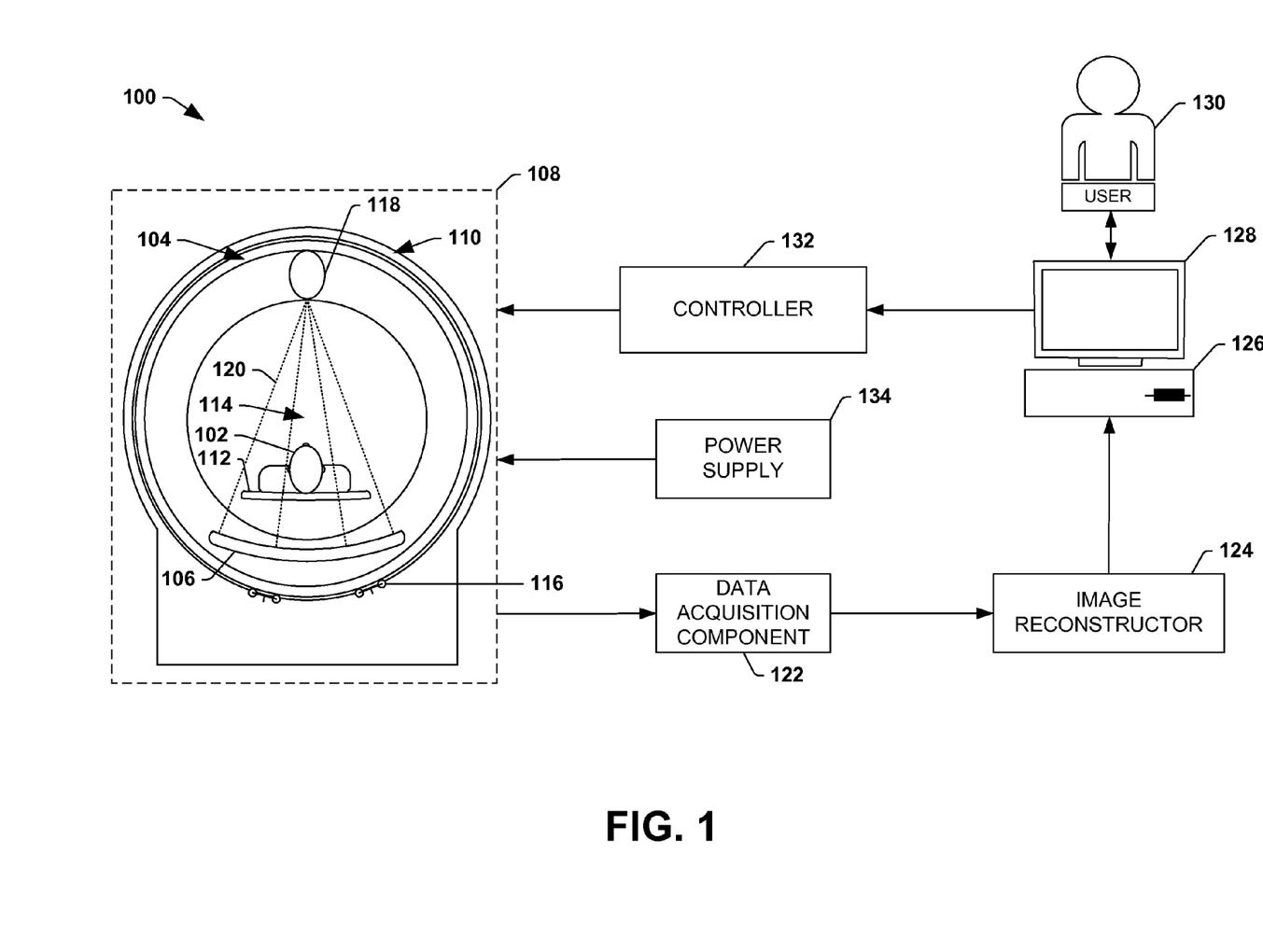
FIG. 1 is a schematic block diagram illustrating an example examination environment for examining an object.

FIG. 1 illustrates an example environment 100 wherein one or more of the techniques and/or systems described herein may find applicability. More particularly, FIG. 1 illustrates an example object examination apparatus comprising a multi-energy CT scanner configured to examine an object(s) 102 (e.g., a patient, suitcase, etc.) at two or more distinct energies (e.g., distinct energy spectrum or levels) by varying a voltage applied to a radiation source 118. It may be appreciated that while specific reference is made herein to using such a power supply to provide power to portions of a CT imaging modality, the instant application may find applicability to other radiation imaging modalities (e.g., such as digital/projection radiology, SPECT, mammography, etc.). Moreover, the disclosure may relate to other fields apart from radiation imaging, such as to fields where a power supply configured to vary an output voltage between two or more voltage levels while providing substantially constant power output may be useful, and the scope of the appended claims is not intended to exclude the same to the extent practical.

In the example environment 100, an examination unit 108 of the imaging modality is configured to examine one or more objects 102. The examination unit 108 can comprise a rotating gantry 104 and a (stationary) support structure 110 (e.g., which may encase and/or surround as least a portion of the rotating gantry 104 (e.g., as illustrated with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise a radiation source 118 (e.g., an ionizing x-ray source, gamma radiation source, etc.) and a detector array 106 that is mounted on a substantially diametrically opposite side of the rotating gantry 104 relative to the radiation source(s) 118. Together, the radiation source 118 and the detector array 106 are configured to capture multi-energy measurements of the object 102. By way of example, the radiation source 118 may be configured to emit radiation at two or more distinct energies. Radiation having a first energy may be emitted when a first voltage (e.g., 60 kV) is applied to the radiation source 118, and radiation having a second energy may be emitted when a second voltage (e.g., 120 kV) is applied to the radiation source 118. Although reference is made herein to first and second energies, it may be appreciated that the source may emit a range of energies at respective voltages (e.g., which a first range or spectra being at least partially distinct from a second range or spectra).

During an examination of the object(s) 102, the radiation source(s) 118 emits fan, cone, wedge, and/or other shaped radiation 120 configurations from a focal spot(s) of the radiation source 118 (e.g., a region within the radiation source 118 from which radiation 120 emanates) into the examination region 114. It may be appreciated that such radiation 120 may be emitted substantially continuously and/or may be emitted intermittently (e.g., a brief pulse of radiation is emitted followed by a resting interval during which the radiation source 118 is not activated). Moreover, the energy of the radiation (e.g., and thus the voltage applied to the radiation source 118) may be toggled between the first energy and the second energy during the examination. For example, in some embodiments, the imaging modality may be configured to operate at 3 kHz, meaning the energy of the radiation is switched between the two energy spectrum every 167 microseconds. However, other operational frequencies for the switching are also contemplated and may depend upon, among other things, a rotational speed of the rotating gantry 104, for example.

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to a data acquisition component 122 configured to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that was emitted while the radiation source 118 was at a particular angular range relative to the object 102. It may also be appreciated that with respect to a multi-energy imaging modality a view is typically comprised of two sub-views, where a first sub-view is representative of data yielded from the radiation emitted at the first energy and a second sub-view is representative of data yielded from the radiation emitted at the second energy. Based upon the compiled signals, the data acquisition component 122 can generate projection data indicative of the compiled signals, for example.

The example environment 100 also illustrates an image reconstructor 124 that is operably coupled to the data acquisition component 122 and is configured to generate one or more images representative of the object 102 under examination based at least in part upon signals output from the data acquisition component 122 using suitable analytical, iterative, and/or other reconstruction technique (e.g., tomosynthesis reconstruction, back-projection, iterative reconstruction, etc.).

The image reconstructor 124 is typically configured to exclude data collected during a transition of the radiation from a first energy to a second energy. As such, it may be desirable to reduce the length of the transition (e.g., to a minimum) when transitioning from radiation having a first energy to radiation having a second energy and/or vice-versa. For example, where the imaging modality operates at 3 kHz as described above, it may be desirable to transition between the two radiation energies in less than 10 microseconds to mitigate the amount of data excluded from the image reconstruction process during the transition. Thus, a power supply 134 may be configured to transition between voltages in less than 10 microseconds, for example.

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination apparatus 108 (e.g., a speed of gantry rotation, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed.

A power supply 134 may be configured to deliver power to at least the radiation source 118. For example, the power supply 134, which may be positioned on a stationary (e.g., or rotating) side of the imaging modality, may be configured to supply power to the radiation source 118 on the rotating side of the imaging modality. Power that is supplied to components on the rotating side of the imaging modality (e.g., coupled to the rotating gantry 104) may be transferred from the support structure 110 to the rotating gantry 104 via a slip-ring assembly and/or a contactless power transfer system, for example.

In one embodiment, as will be described in more detail below, the power supply 134 may be configured to provide a substantially constant power output while varying the voltage that is applied to the radiation source 118. In this way, more photons may be emitted at a lower voltage and a statistical increase in photon count at detector array 106 may be realized which may improve a signal-to-noise ratio (e.g., at least relative to conventional dual-energy imaging modalities, wherein fewer photons are emitted at lower voltages because power output typically drops when switching from a high voltage output to a lower voltage output, for example).

Figure 2:
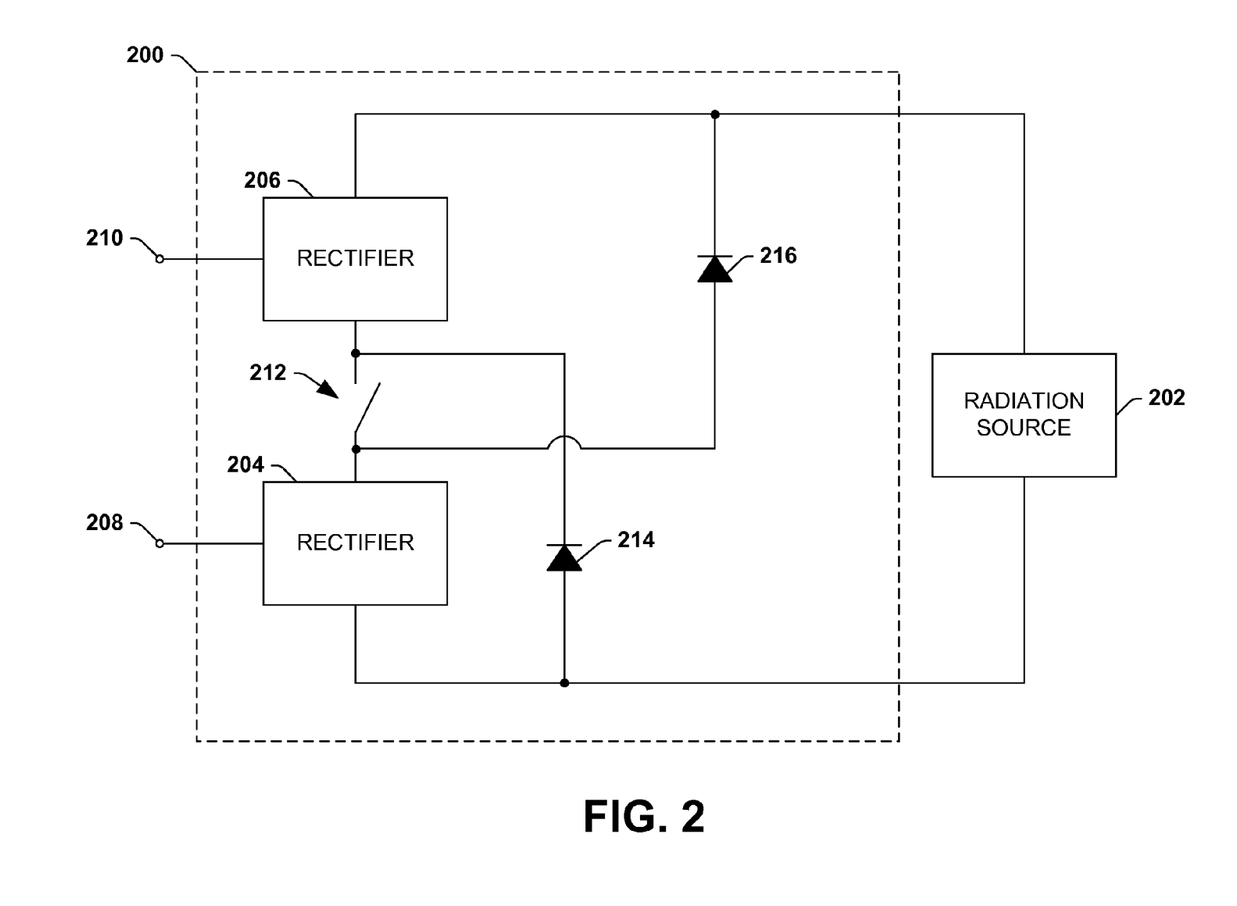
FIG. 2 is an example arrangement of a power supply configured to provide power to a radiation source.

FIG. 2 illustrates an example power supply 200 (e.g., 134 in FIG. 1) operably coupled to a radiation source 202 (e.g., 118 in FIG. 1) and configured to vary a voltage applied to the radiation source 202 by the power supply 200 between two or more voltages while substantially maintaining a constant power output to the radiation source 202. More particularly, the power supply 200 is configured to vary a current of an electrical signal output by the power supply 200 (and supplied to the radiation source 202) indirectly and proportionally with a voltage that is applied to the radiation source by the power supply 200. Thus, when the voltage output by power supply 200 is doubled, the current of the electrical signal is reduced by half to maintain a substantially constant power output. When the voltage output by the power supply 200 is reduced by half, the current of the electrical signal is doubled, for example. In this way, by varying the current indirectly with the voltage, substantially constant power may be output by the power supply 200 during a transition between different voltages, for example.

As illustrated, the power supply 200 comprises two rectifiers 204, 206 respectively configured to receive an alternating current (AC) electrical signal at input nodes 208, 210 and to convert the AC electrical signal to a direct current (DC) electrical signal. By way of example, the rectifiers 204, 206 may be full-bridge rectifiers or half-bridge-rectifiers. Typically, respective rectifiers 204, 206 are high voltage rectifiers configured to output a voltage in the kilovolt range. However, one or more rectifiers may be configured to output a lower voltage.

The output of respective rectifiers 204, 206 is generally substantially similar in current and/or in voltage. For example, in one embodiment, respective rectifiers 204, 206 are configured to output a voltage of about 90 kV at a current of approximately 40 mA. In this way, the rectifiers 204, 206 may be comprised of substantially similar electrical components and/or properties of the AC electrical signal input to respective rectifiers 204, 206 may be substantially similar.

The power supply 200 is configured to vary the voltage applied to the radiation source 202 by switching the at least two rectifiers 204, 206 between a parallel arrangement and a series arrangement. For example, in the illustrated embodiment, the power supply 200 comprises a switching component 212 electrically arranged between a first rectifier 204 and a second rectifier 206 and configured to switch the two rectifiers 204, 206 between a parallel arrangement and a series arrangement. When the switching component 212 is open, diodes 214, 216 of the power supply 200 may be forward biased, effectively causing the first rectifier 204 to be in parallel with the second rectifier 206. When the switching component 212 is closed, the diodes 214, 216 may be reverse or backward biased, effectively causing the first rectifier 204 to be in series with the second rectifier 206 (e.g., causing the voltage output by the first and second rectifiers 204 to be combined).

In an embodiment where the first and second rectifiers are configured to output substantially similar currents and voltages, it may be appreciated that the effect of arranging the rectifiers 204, 206 in parallel may be to decrease the voltage applied to the radiation source 202 by half while doubling the current supplied to the radiation source 202 by the power supply 200 (e.g., relative to the voltage/current applied/supplied when the rectifiers 204, 206 are in series). In this way, the power output by the power supply 200 may remain substantially constant while the voltage applied to the radiation source 202 by the power supply 200 is varied, for example. By way of example, where the rectifiers 204, 206 are respectively configured to output approximately 90 kV and are arranged in parallel, the voltage output by the power supply may be approximately 90 kV and the output current may be approximately 40 mA. When the arrangement of the rectifiers is switched from a parallel arrangement to a series arrangement the voltage output by the power supply 200 may be approximately 180 kV while the output current may be approximately 20 mA. It may be appreciated that doubling the current output by the power supply 200 when the rectifiers 204, 206 are arranged in parallel may have little to no effect on a high frequency ripple in the signal because filter capacitance may be doubled, for example, with the doubling of the current and/or the reduction in voltage. Moreover, the charge in capacitors comprised within one of more of the rectifiers 204, 206 may be conserved during the voltage transition. Therefore, energy losses during the transition may be negligible, for example.

The degree to which the voltage is varied and/or the frequency with which it is varied may be a function of, among other things, configurations of respective rectifiers 204, 206, and/or the intended application of the power supply 200. By way of example, in imaging applications where the rotating gantry is rotating at a high RPM, the voltage may be varied by 60 or more kilovolts and the frequency with which the voltage is varied may be in the range of 500 hertz or more (e.g., and may exceed 3 kHz). Thus, for example, the voltage applied to the radiation source 202 by the power supply 200 may be switched between a first voltage and a second voltage every 167 microseconds during an examination when the imaging modality is configured to operate at 3 kHz, for example.

It may also be appreciated that while the example power supply 200 merely comprises two rectifiers, in another embodiment, the power supply 200 may comprise more than two rectifiers. As described herein, respective rectifiers may be electrically separated by a switching component, for example, such that that arrangement of rectifiers may be switched between parallel and series. By way of example, a power supply may comprise four rectifiers, with each rectifier separated by a switching component. In such an embodiment numerous different arrangements are contemplated. For example, the four rectifiers may be in parallel; a first set of two rectifiers may be arranged in parallel and a second set of two rectifiers may be arranged in parallel with the two parallel arrangements being arranged in series; and/or the four rectifiers may be arranged in series. Moreover, a switching component may merely electrically separate some, but not all, of the rectifiers. Thus, some rectifiers may be permanently arranged in series or parallel while the arrangement of other rectifiers is switched from time-to-time.

The switching component 212 is configured to support at least the voltage output by the first rectifier 204. For example, in one embodiment, the first rectifier 204 is configured to output a voltage of 60 kV. As such, the switching component is configured to support a voltage of at least 60 kV (e.g., although it may be desirable to support a voltage that is greater than the voltage applied to the switching component 212 by the first rectifier 204 to provide increased margins). Given technical and/or cost considerations, it may be impractical for a single switch to support such a voltage. As such, the switching component 212 may be comprised of a plurality of switches as illustrated with respect to FIGS. 3 and 4 (e.g., where respective switches may be capable of supporting a portion of the total voltage output by the first rectifier 204).

Figure 3:
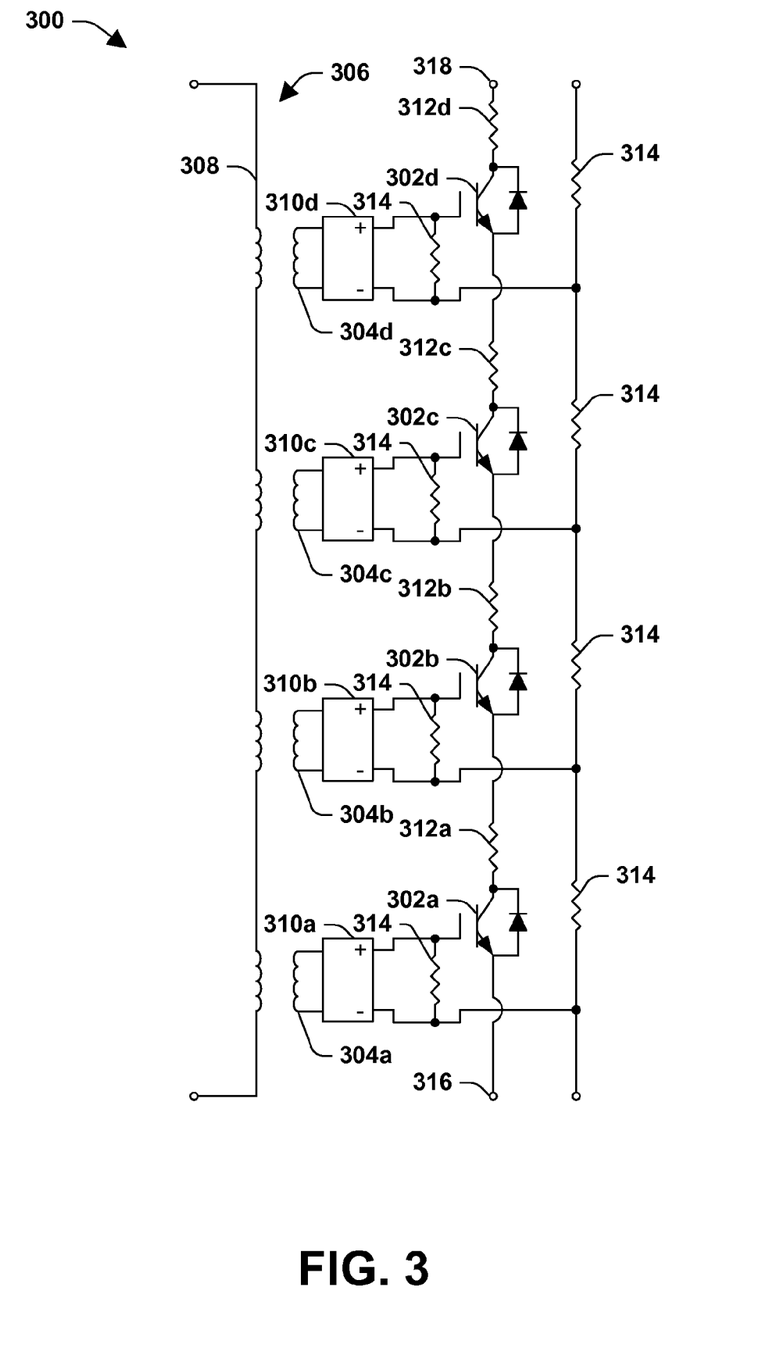
FIG. 3 illustrates a schematic of an example switching component.
Figure 4:
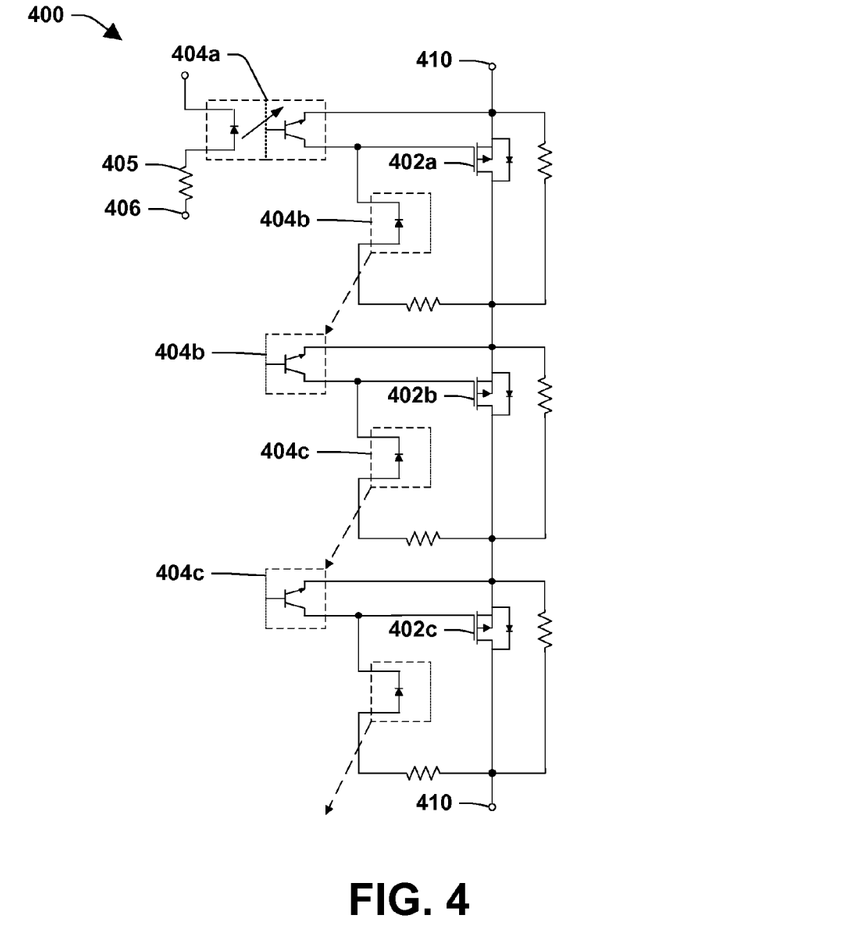
FIG. 4 illustrates a schematic of an example switching component comprising a plurality of optical control circuits.

It may be appreciated that FIGS. 3-4 are merely intended to provide example arrangements of a switching component 212. As such, the instant application, including the scope of the claims, is not intended to be limited to such arrangements to the extent practical. Moreover, others devices and/or techniques besides those described herein may be utilized to selectively arrange rectifiers in series and/or in parallel. For example, FIGS. 3-4 describe transistors as being utilized to perform the switching. However, other circuit components for performing such switching are also contemplated, and for purposes of simplicity the term transistor and switch may be utilized interchangeably (e.g., to describe any of the numerous circuit components that are capable of performing switching).

FIG. 3 illustrates an example switching component 300 comprised of a plurality of transistors 302a-d (e.g., which behave as switches) respectively coupled to an isolated portion of a secondary winding 304a-d of a transformer 306 (e.g., illustrated via the secondary windings 304a-d and a primary winding 308). An electrical signal input into the primary winding 308 of the transformer 306 induces an AC switching signal in respective secondary windings 304a-d that, in turn, cause the transistors 302a-d respectively electrically coupled thereto to (concurrently or simultaneously) switch between an open and a closed state. For example, a first AC switching signal induced in a first secondary winding 304a may be configured to cause a first transistor 302a to switch between an open and a closed state; a second AC switching signal induced in a second secondary winding 304b may be configured to cause a second transistor 302b to switch between an open and a closed state (e.g., concurrently with the first secondary winding 304a switching the first transistor 302a between an open and closed state), etc. Current output by a first rectifier (e.g., 204 in FIG. 2) may be supplied to respective transistors 302a-d via an input node 316, and current flowing through the transistors when the transistors 302a-d are closed may be output to a second rectifier (e.g., 206 in FIG. 2) via output node 318.

To transition respective transistors 302a-d between an open state and a closed state, one or more properties of the electrical signal input to the primary winding 308 may be varied (e.g., causing similar properties in respective AC switching signals to change). For example, when there is a desire to open respective transistors 302a-d, current may be passed through the primary winding 308. When there is a desire to close respective transistors 302a-d, current to the primary winding 308 may be turned off, for example. Alternatively, the transistors 302a-d may be closed when current is received at the transistors 302a-d from the primary winding 308 (through respective secondary windings 304a-d) and may be opened when little to no current is provided in the primary winding 308.

It may be appreciated that the switching signals induced at respective secondary windings 304a-d of the transformer 306 are alternating current signals and the transistors 302a-d may be configured to receive merely direct current signals. As such, in one embodiment, the switching component 300 further comprises a plurality of rectifiers 310a-d (e.g., which may be referred to as switching rectifiers so as not to be confused with the high voltage rectifiers described with respect to FIGS. 2-3). As illustrated, respective switching rectifiers 310a-d are electrically arranged between the isolated secondary windings 304a-d and respective transistor 302a-d and are configured to convert the AC switching signal to a DC switching signal.

The example switching component 300 further comprises voltage dividers, such as resistive dividers (e.g., resistors 312a-d) configured to electrically isolate respective transistors 302a-d (e.g., switches). For example, a first transistor 302a may be isolated from other transistors 302b-d of the plurality of transistors via a voltage divider. In this way, the total voltage of the switching component 300 may be partitioned across a plurality of transistors 302a-d, for example, to reduce the possibility of the total voltage (e.g., which may exceed 60 kV) being applied to a single transistor, for example.

The example switching component 300 further comprises a plurality of other resistors 314 configured to smooth the waveform produced by respective rectifiers 310a-d, to scale the waveform as desired, and/or to control the flow of current through the switching component 300, for example, to further reduce and/or mitigate damage to the transistors 302a-d that may be caused by an excessively high voltage (e.g., that respective transistors 302a-d are not configured to support) being applied thereto, for example.

It may be appreciated that the transistors 302a-d may be switched substantially concurrently by using a switching component 300 comprising a primary winding 308 and a plurality of secondary windings 304a-d. That is, a current flowing through the primary winding 308 may generate switching signals in respective isolated secondary windings 304a-d substantially concurrently (e.g., although there may be some delay in the switching of one transistor relative to the switching of other transistors due to manufacturing variations in the windings, rectifiers, and/or transistors, for example).

In another embodiment, instead of switching the transistors concurrently and/or simultaneously, the transistors may be switched in a cascading manner (e.g., starting from a 0 volt transistor (e.g., electrically nearest the input of the switching component) and moving upwards or starting with a highest volt transistor (e.g., electrically nearest the output of the switching component) and moving downwards. FIG. 4 illustrates an example embodiment of a switching component 400 (e.g., 212 in FIG. 2) comprised of a plurality of transistors 402a-c that are configured to be opened/closed in a cascading manner (e.g., a first transistor 402a is opened, and then a second transistor 402b is opened after the first transistor 402a is opened, etc.). Current output by a first rectifier (e.g., 204 in FIG. 2) may be received at input node 408 and current flowing through the transistors 402a-c (e.g., from the first rectifier) may be output to the second rectifier (e.g., 206 in FIG. 2) at output node 410.

More particularly, the example switching component 400 is comprised of a plurality of optical control circuits 404a-c respectively coupled to a transistor 402a-c (e.g., 302 in FIG. 3). In the illustrated embodiment, the transistors 402a-c are configured to be transitioned from a first state to a second state in a cascading manner. By way of example, an initial signal (e.g., a control signal) may be transmitted to a first optical control circuit 404a via input node 406 (e.g., optionally coupled through a resistor 405), which may cause the first optical control circuit 404a to generate a switching signal configured to notify the electrically coupled transistor 402a to transition states (e.g., from an open state to a closed state and/or from a closed state to an open state). The switching signal generated by the first optical control circuit 404a may also be transmitted to a second optical control circuit 404b, causing the second optical control circuit 404b to generate a switching signal configured to notify the electrically coupled transistor 402b to transition states. Thus, the switching signal generated by respective optical control circuits 404a-b may be configured to cause an electrically coupled transistor 402a-b, respectively, to transition state, and to provide notice to an electrically adjacent optical control circuit 504b-c to generate a switching signal. It may be appreciated that, in the illustrated example, optical control circuit 504c merely outputs a switching signal generated thereby to a transistor 504c (e.g., and not to another optical control circuit) because the optical control circuit 504c is the last control circuit in the chain, for example.

It may be appreciated that for purposes of brevity, like features, described with respect to FIG. 3, such as the arrangement of resistors and/or diodes are not described with respect to FIG. 4. However, as illustrated, such components may exist to control the flow of current and/or to control the voltage applied to respective transistors 402a-c, for example.

Figure 5:
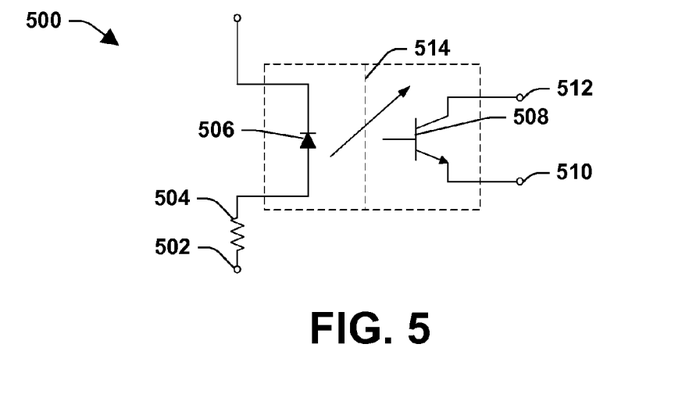
FIG. 5 illustrates a schematic of an example optical control circuit.

FIG. 5 illustrates a schematic of an example optical control circuit 500 (e.g., 404a-c in FIG. 4) that may be used to control a transistor (e.g., 402a-c in FIG. 4) of a switching component (e.g., 400 in FIG. 4) that is configured to selectively arrange two or more rectifiers (e.g., 204, 206 in FIG. 2) in series or parallel, for example. Such a circuit 500 may also be referred to as an opto-isolator circuit for reasons at least described below.

The example optical control circuit 500 comprises input node 502 (e.g., 406 in FIG. 4) configured to receive an input signal from a power supply (e.g., such as a DC power supply), for example. In the example schematic, a resistor 504 is coupled to the input node 502 and is configured to provide a predetermined level of resistance. In this way, the resistor 504 provides protection against currents or voltages that exceed a predetermined threshold, for example.

The example optical control circuit 500 also comprises a light-emitting diode (LED) 506. When the LED 506 is forward biased (e.g., switched on), energy may be emitted from the diode in the form of light, for example. When the LED 506 is reverse or backward biased (e.g., switched off), no light may be emitted, for example.

Light emitted from the LED 506 may be detectable by a photosensitive transistor 508. The photosensitive transistor 508 is configured to switch signals depending upon whether light is or is not detected. For example, when no light is emitted from the LED 506, the photosensitive transistor 508 may allow current to flow from a first node 510 (e.g., 408 in FIG. 4) to a second node 512 (e.g., which may be transmitted to a transistor (e.g., 402a-c in FIG. 4) to cause the transistor to open, for example). When light is emitted, the photosensitive transistor 508 may detect the light and close the switch, causing the flow of current to the second node 512 to stop (e.g., causing the transistor electrically coupled to the second node 512 to act as a switch that is open, for example). Thus, a photosensitive transistor 508 may open and/or close (e.g., to allow or prevent a switching signal to flow through the photosensitive transistor 508) as a function of detected light, and a transistor (e.g., 402a-c in FIG. 4) of the switching component may open or close based upon whether the switching signal is detected or not detected, for example.

It may be appreciated that a dashed line 514 represents an isolation barrier. Such an isolation barrier is useful because it can provide a desired degree of electrical isolation, for example. That is, it may reduce, or prevent, electrical contact between the input node 502 and the nodes 510, 512 that are coupled to the photosensitive transistor 508, for example.

Figure 6:
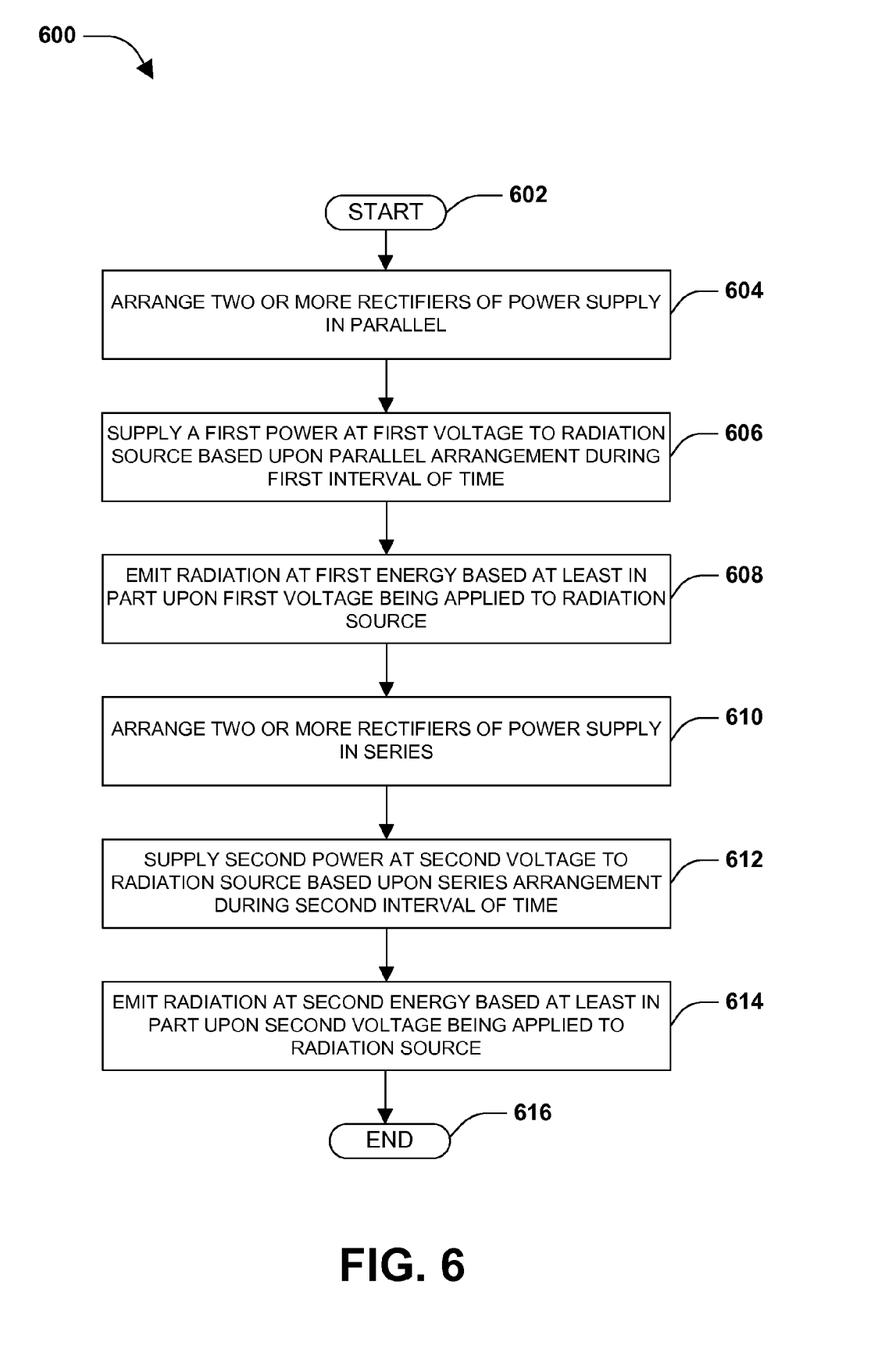
FIG. 6 is a flow diagram illustrating an example method for emitting radiation at at least two different energies from a radiation modality.

FIG. 6 illustrates an example method 600 for emitting radiation from a radiation source. During a first interval of time (e.g., which may be in the microsecond to milliseconds range) radiation may be emitted at a first energy and during a second interval of time (e.g., which may also be in the microsecond to milliseconds range) radiation may be emitted at a second, different energy. In this way, by toggling the energy of radiation emitted from a radiation source between at least two different energies, or energy spectrum, multi-energy measurements of an object under examination can be performed from which a density and/or z-effective image(s) of the object may be generated, for example. Such a method 600 may find particular applicability with respect to multi-energy CT scanners and/or line scanners where a single radiation source may be configured to emit radiation at any multiple energy spectrum by varying a voltage applied to the radiation source, for example.

The example method 600 begins at 602 and two or more rectifiers of a power supply are arranged in parallel at 604. For example, as described with respect to FIG. 2, the power supply may be comprised of, among other things, two or more rectifiers, at least one switching component, and a plurality of diodes configured to, among other things, control the flow of current in the power supply. When the switching component, electrically arranged between at least two of the two or more rectifiers, is opened, for example, one or more diodes of the power supply may become forward biased, effectively causing the at least two rectifiers to be arranged in parallel.

At 606 in the example method 600, a first power is supplied at a first voltage to the radiation source based upon the parallel arrangement during a first interval of time (e.g., for 150 microseconds). Power is the product of the output current and output voltage. When the rectifiers are arranged in parallel, the output current is typically the sum of the currents output by respective rectifiers and the output voltage is approximately the average voltage output by rectifiers arranged in parallel.

In one embodiment, respective rectifiers are configured to output a substantially same voltage and substantially same current. As such, when the power supply comprises merely two rectifiers, with respective rectifiers being arranged in parallel, the current output by the power supply may be approximately two times the current output by respective rectifiers and the voltage may be approximately equal to the voltage output by respective rectifiers. However, the voltage and/or current may differ from these example figures if respective rectifiers are configured to output different currents and/or voltages and/or if the power supply comprises more than two rectifiers, for example.

At 608 in the example method 600, radiation is emitted at a first energy based at least in part upon the first voltage being applied to the radiation source. That is, stated differently, the energy of the radiation is typically a function of the voltage applied to the radiation source. The higher the voltage, the higher the energy of the radiation. As such, the energy emitted when the first voltage is applied to the radiation source (e.g., when the two or more rectifiers of the power supply are arranged in parallel) may be different than the energy emitted when a second, different voltage is applied to the radiation source, for example.

After a desired/specified interval of time (e.g., after the first interval of time has elapsed), the two or more rectifiers of the power supply (e.g., arranged in parallel at 604) may be arranged in series at 610 in the example method 600. By way of example, the switching component may be switched from an open state to a closed state, causing one or more diodes of the power supply to be back biased, such that the two or more rectifiers are switched from a parallel arrangement to a series arrangement.

It may be appreciated that by changing the arrangement of the rectifiers, the voltage output by the power supply may be changed without changing the voltage and/or current output by respective rectifiers. As such, energy stored within capacitors of respective rectifiers may be maintained while varying the voltage output by the power supply, for example. That is, stated differently, capacitors comprised within one or more rectifiers may be charged upon an initial input of an electrical signal into the rectifiers and may remain charged while varying the voltage applied to the radiation source by respective rectifiers (e.g., by switching the arrangement of two or more rectifiers between a parallel arrangement and a series arrangement).

At 612 in the example method 600, second power is supplied at a second voltage to the radiation source based upon the series arrangement of the two or more rectifiers during a second interval of time. That is, stated differently, a different voltage is applied to the radiation source, relative to the voltage applied to the radiation source during the first interval of time, and at 614 in the example method 600, radiation is emitted at a second energy based at least in part upon the second voltage being applied to the radiation source.

It may be appreciated that, depending upon the output of respective rectifiers, in one embodiment, the second power supplied while the rectifiers are in series may be equal to the first power supplied while the rectifiers are in parallel. By way of example, when the rectifiers are configured to output similar voltages and currents, the current output by the power supply may be reduced in half when the rectifiers are in series relative to the current output when the rectifiers are in parallel. Moreover, the voltage output by the power supply when the rectifiers are in series may be substantially doubled relative to the voltage output when the rectifiers are in parallel. As such, that power output by the power supply may remain substantially constant when the rectifiers are switched from a parallel arrangement to a series arrangement.

The example method 600 ends at 616.

Figure 7:
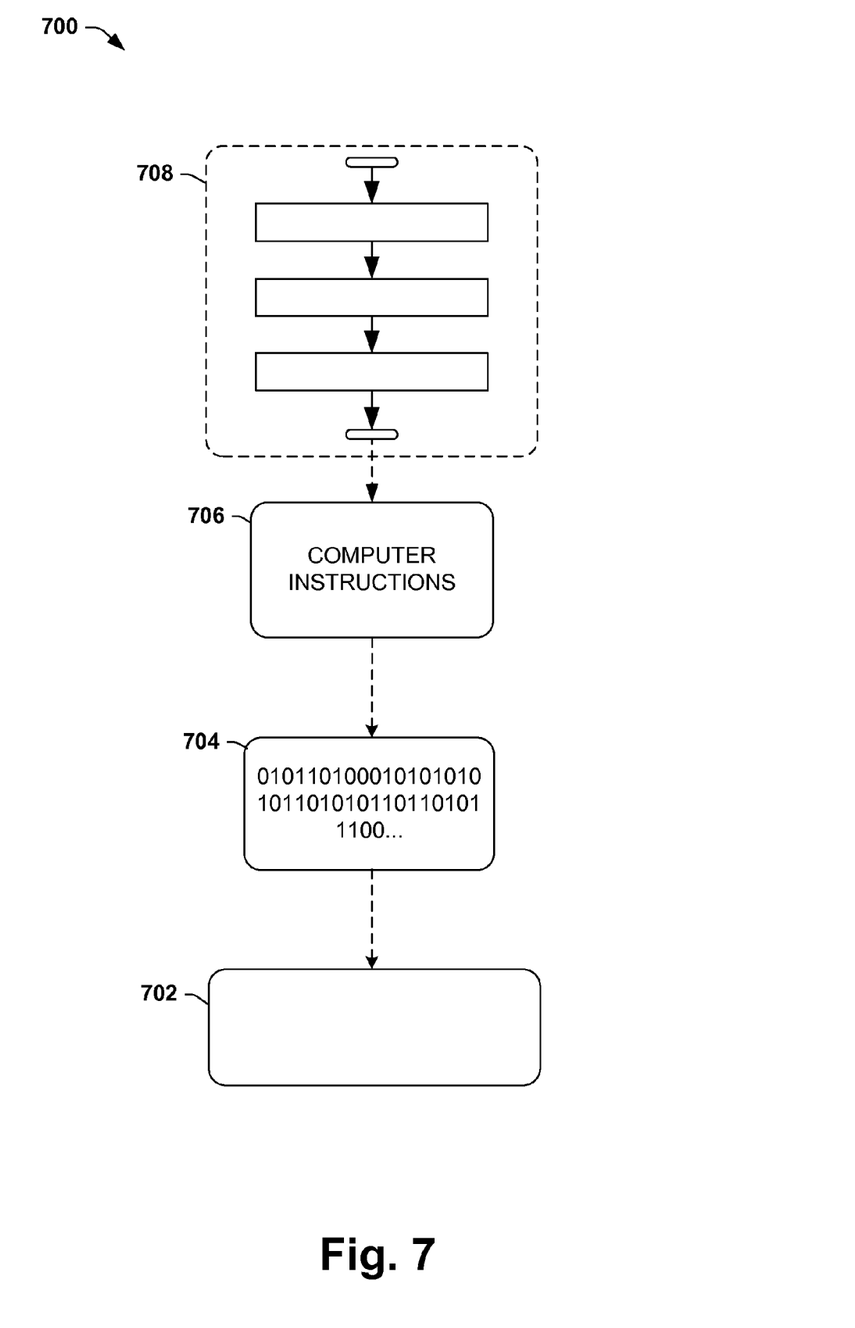
FIG. 7 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 7, wherein the implementation 700 comprises a computer-readable medium 702 (e.g., a CD-R, DVD-R, or a platter of a hard disk drive), on which is encoded computer-readable data 704. This computer-readable data 704 in turn comprises a set of computer instructions 706 configured to operate according to one or more of the principles set forth herein. In one such embodiment 700, the processor-executable instructions 706 may be configured to perform a method 708, such as the example method 600 of FIG. 6, for example. In another such embodiment, the processor-executable instructions 706 may be configured to implement a system, such as at least some of the exemplary scanner 100 of FIG. 1 and/or exemplary system 200 of FIG. 2, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B and/or the like generally means A or B or both A and B.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A power supply configured to provide power to at least a radiation source of a radiation imaging modality, the power supply comprising:
    at least two rectifiers; and
    a switching component configured to vary a voltage applied to the radiation source by switching the at least two rectifiers between a parallel arrangement and a series arrangement, the power supply configured to substantially maintain a constant power output to the radiation source while varying the voltage applied to the radiation source such that the radiation source emits radiation at a first energy when a first voltage is applied to the radiation source and emits radiation at a second energy when a second voltage is applied to the radiation source.

2. The power supply of claim 1, at least one rectifier of the at least two rectifiers comprising a capacitor, the capacitor remaining substantially charged while varying the voltage applied to the radiation source.

3. The power supply of claim 1, the switching component configured to support a voltage of at least 60 kV.

4. The power supply of claim 1, the switching component comprising a plurality of switches, respective switches coupled to an isolated secondary of a transformer configured to provide a switching signal to respective switches.

5. The power supply of claim 4, a first switch isolated from other switches of the plurality of switches via a voltage divider.

6. The power supply of claim 1, the switching component comprising a plurality of optical control circuits.

7. The power supply of claim 6, the plurality of optical control circuits respectively comprising a photosensitive transistor.

8. The power supply of claim 1, varying the voltage applied to the radiation source comprising varying the voltage between the first voltage and the second voltage at a frequency of at least 500 Hz.

9. The power supply of claim 1, the first voltage approximately one-half of the second voltage.

10. A method for emitting radiation at at least two different energies from a radiation modality, comprising:
    arranging two or more rectifiers of a power supply in parallel;
    supplying a first power at a first voltage to a radiation source based upon the parallel arrangement during a first interval of time;
    emitting radiation at a first energy based at least in part upon the first voltage being applied to the radiation source;
    arranging the two or more rectifiers of the power supply in series;
    supplying a second power at a second voltage to the radiation source based upon the series arrangement during a second interval of time; and
    emitting radiation at a second energy based at least in part upon the second voltage being applied to the radiation source.

11. The method of claim 10, the first power substantially equal to the second power.

12. The method of claim 10, arranging the two or more rectifiers of the power supply in series comprising closing a switching component to cause the two or more rectifiers to switch from the parallel arrangement to the series arrangement.

13. The method of claim 12, the switching component configured to support a voltage of at least 60 kV.

14. The method of claim 12, the switching component comprising at least one of an isolation transformer switch or an optical control circuit.

15. The method of claim 10, comprising:
    charging a capacitor comprised within at least one of the two or more rectifiers prior to supplying the first power; and
    maintaining the charge of the capacitor while transitioning to supply the second power.

16. The method of claim 10, at least one of first voltage or the second voltage being at least 60 kV.

17. The method of claim 10, at least one of:
    the first interval of time not exceeding 500 microseconds, or
    the second interval of time not exceeding 500 microseconds.

18. A multi-energy imaging modality, comprising:
    a radiation source configured to emit radiation;
    a detector array configured to detect at least some of the emitted radiation that has traversed an object under examination; and
    a power supply configured to provide power to at least the radiation source, the power supply comprising:
        at least two rectifiers; and
        a switching component configured to vary a voltage applied to the radiation source by switching the at least two rectifiers between a parallel arrangement and a series arrangement, the power supply configured to substantially maintain a constant power output while varying the voltage applied to the radiation source during an examination of the object.

19. The multi-energy imaging modality of claim 18, the switching component configured to support a voltage of at least 60 kV.

20. The multi-energy imaging modality of claim 18, the radiation source comprising an ionizing radiation source.

* * * * *